US010837960B2

(12) United States Patent
Martinez et al.

(10) Patent No.: US 10,837,960 B2
(45) Date of Patent: Nov. 17, 2020

(54) ASSAY DEVICES AND METHODS

(71) Applicant: Cal Poly Corporation, San Luis Obispo, CA (US)

(72) Inventors: Nathaniel Martinez, Arroyo Grande, CA (US); Andres Martinez, Pismo Beach, CA (US)

(73) Assignee: CALIFORNIA POLYTECHNIC STATE UNIVERSITY, San Luis Obispo, CA (US)

( * ) Notice: Subject to any disclaimer, the term of this patent is extended or adjusted under 35 U.S.C. 154(b) by 924 days.

(21) Appl. No.: 15/238,315

(22) Filed: Aug. 16, 2016

(65) Prior Publication Data
US 2018/0052155 A1 Feb. 22, 2018

(51) Int. Cl.
*G01N 33/543* (2006.01)
*G01N 33/52* (2006.01)
*G01N 33/58* (2006.01)

(52) U.S. Cl.
CPC .......... *G01N 33/54333* (2013.01); *C12Y 304/21004* (2013.01); *C12Y 304/21009* (2013.01); *G01N 33/54306* (2013.01); *G01N 33/54326* (2013.01); *G01N 2333/96441* (2013.01); *G01N 2333/976* (2013.01)

(58) Field of Classification Search
CPC ....... C12Q 1/37; G01N 33/581; G01N 33/525
See application file for complete search history.

(56) References Cited

U.S. PATENT DOCUMENTS

2010/0279394 A1\* 11/2010 Bocking ................ H01L 33/06
435/287.1
2015/0005193 A1 1/2015 Phillips

OTHER PUBLICATIONS

Gregory G. Lewis and Scott T. Phillips, Quantitative Point-of-Care (POC) Assays Using Measurements of Time as the Readout: A New Type of Readout for mHealth, 2015, Methods in Molecular Biology, vol. 1256, pp. 213-229. (Year: 2015).\*
Ionescu, R. E. et al., Protease Amperonnetric Sensor, 2006, Analytical Chemistry, vol. 78, No. 18, pp. 6327-6331. (Year: 2006).\*

\* cited by examiner

*Primary Examiner* — Tracy Vivlemore
*Assistant Examiner* — Nam P Nguyen
(74) *Attorney, Agent, or Firm* — McKee, Voorhees & Sease, PLC

(57) ABSTRACT

An assay device including a loading zone for a sample that may contain an analyte, an activator in communication with the loading zone from which at least one activator is displaced by presence of the analyte, an amplifier in an inactive state in communication with the activator that becomes activated in the presence of the activator, a biomatrix barrier in communication with the activated amplifier that is degraded or modified by the activated amplifier, and an indicator responsive to the degradation or modification of the biomatrix barrier, which in turn reflects a concentration of the analyte in the sample loaded on the device. The selection of analyte or displacement of the activator by presence of the analyte may occur off-platform and/or may rely on use of non-covalent interactions. The activator may include an enzyme or other reagent that activates the amplifier. Also, associated methods.

30 Claims, 3 Drawing Sheets

ASSAY DEVICES AND METHODS

BACKGROUND

The present disclosure generally relates to assay devices and methods involving degradation or modification of biological matrices.

SUMMARY

Aspects of the subject technology include an assay device and method. In some aspects, the device includes a loading zone for a sample. The loading zone may contain an activator, which may be displaced as a function of the concentration of analyte present in the sample. In communication with the loading zone is an inactive-amplifier, which becomes active in response to the activator. In communication with the amplifier, now in its active form, is a biomatrix barrier that may be chemically or conformationally modified by the amplifier. In communication with the biomatrix barrier is an indicator responsive to the alteration of the barrier. The activator may be an enzyme, the amplifier may include a zymogen, and the biomatrix barrier may be a biopolymer that forms an aqueos impermeable or semipermeable barrier such as gelatin In some aspects of the device, the displacement of the activator may be performed outside of the loading zone, either on an additional zone on the device or off-platform prior to addition of sample to the loading zone.

The activator may include enzymes that activate zymogens such as enterokinase. The activator may be immobilized and then displaced via disruption of covalent or non-covalent interactions, such as immunoselection, DNA hybridization, aptamer selection, covalent linkages or magnetic affinity. The amplifier may include zymogens such as Trypsinogen or other reagents that can exist in an inactive state and then be activated upon interacting with the activator.

In some aspects, the loading zone, the activator, the amplifier, the biomatrix barrier, the indicator, or some combination thereof are disposed on paper or other porous membrane layers. A frame may be included to hold the layers in communication with each other.

The assay device may include one or more additional loading zones, associated activators and selection reagents, associated amplifiers, associated biomatrix barriers, or associated indicators. These additional elements may be calibrated to respond to varying concentrations of the analyte present in the sample.

The subject technology also includes methods associated with using the foregoing devices.

This brief summary has been provided so the nature of the invention may be understood quickly. Additional steps and/or different steps than those set forth in this summary may be used. A more complete understanding of the invention may be obtained by reference to the following description in connection with the attached drawings.

DETAILED DESCRIPTION

Figure 1:
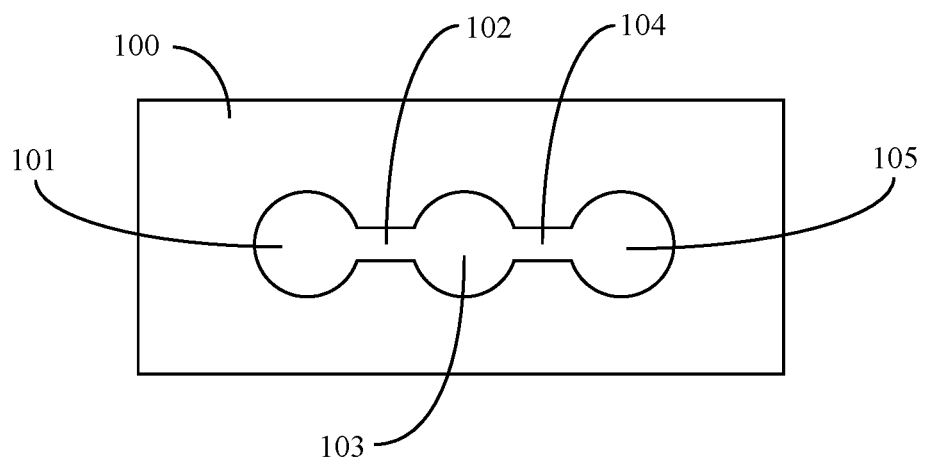
FIG. 1 illustrates aspects of the subject technology arranged in a generally two-dimensional structure.

Briefly, aspects of the subject technology include a new method for quantitatively measuring femtomolar or higher concentrations of analytes in solution using a simple paper-based assay. The technology may be implemented with a device made out of paper, broadly defined as any porous membrane or substrate, with at least three distinct zones in series. The zones may be arranged either along a channel on a single layer of paper or on three or more separate layers of paper that are then stacked on top of each other. Other arrangements are possible.

As background, one objective of the subject technology is to enable a modest, cost-effective, home-use diagnostic device for the reliable quantitation of female reproductive hormones at low-picomolar concentrations using paper-based biomatrices. A fundamental challenge of the 21st century continues to be the empowerment of women worldwide to take control of their reproductive health, their reproductive security and family planning, irrespective of their economic means. Paper based diagnostic tests (e.g., microPADs) are emerging as inexpensive, portable, and reliable alternatives to current laboratory-based methods for detecting and quantitating human biomarkers, such as a panel of female reproductive hormones, in resource-limited settings.

The significance of a diagnostic device that has potential for providing women (and healthcare professionals/researchers) with quantitative data in real-time about their natural hormonal fluctuations from the advent of puberty to the onset of menopause and beyond may be incalculable. The implications of such a device extend deep into a woman's family planning, both as a tool for conception and contraception. A device according to aspects of the subject technology also has significant implications for a woman's reproductive health and security by providing real-time data about their natural hormonal fluctuations and abnormalities. The ability to compile data on measurements of reproductive health markers, at this scale, may allow health professionals, researchers, and policy makers to make informed decisions about policy changes and medical recommendations at global levels.

The subject technology is not limited to the foregoing objectives and uses. Rather, the technology may also be useful for detecting other analytes in a vast number of different contexts. For example and without limitation, the technology may be used to detect proteins, nucleic acids, small molecules, steroid and/or non-steroid hormones, enzymes, antibodies, genetic markers, disease markers, and other analytes.

Aspects of the subject technology include a preferably paper-based microfluidic device capable of: (i) the selection of hormones or other analytes from microliter quantities of blood, urine, saliva or other samples, resulting in (ii) the degradation or modification of biologically derived matrixes followed by (iii) a signal correlating to temporal hormone concentrations in-vivo, triggering (iv) a read-out that may be easily interpreted with simple instructions. The potential advantages of this subject technology include but are not limited to the following: (i) amenability to a modular design where several dozen assays may be performed simultaneously on a single device, (ii) detection of a range of different types of analytes, (iii) requirement for only a small sample volume, (iv) simplicity of operation preferably requiring only one sample-addition step, (v) delivery of a simple readout, and (vi) determination of femtomolar concentrations of analytes, which may enable measurement of certain human hormones that otherwise may not be detectable.

The subject technology may be embodied in a preferably simple device for the detection and quantitation of a myriad of female reproductive hormones and/or other analytes at femtomolar concentrations. Examples of such hormones include but are not limited to 17-β-Estradiol, Progesterone, Leutinizing hormone (LH), Follicle stimulating hormone (FSH), Gonadotropin releasing hormone (GnRH), and beta-human chorionic gonadotropin hormone (β-HCG). Examples of other analytes include but are not limited to protein markers such as interleukins, antibodies and receptors. Further examples include but are not limited to small molecules such as lipids, glycosides, alkaloids, terpenes and phenols, as well as oligonucleotides of various sizes of DNA or RNA such as aptamers.

Aspects of the subject technology include and/or may be implemented via coating paper layers with various substances using a printer, for example a laser or inkjet printer. The printer may be used to form a water-impermeable coating on microPADs. Toner or other substances generated by a printer may be used as a thermal adhesive to bond multiple layers of paper together in order to create 3D microPADs.

As mentioned above, aspects of the subject technology may be embodied using paper. Potential advantages of using paper include the following: Paper is inexpensive, wicks fluids by capillary action (e.g., wicking), and may provide a large surface area for immobilizing and storing reagents.

Unlike conventional microfluidic devices, microPADs wick fluids by capillary action so they do not require any pumps, power sources, or other supporting equipment to function. Of course, such may be used if so desired.

Aspects of the subject technology may be enabled by other technologies that allow for the fabrication of microPADs via patterning paper into a network of hydrophilic channels and test zones bounded by hydrophobic barriers. The patterning process preferably defines the width and length of channels, and paper thickness preferably defines height and/or temporal aspects of the channel.

Photolithography was used in initial development of aspects of the disclosed assay devices. The subject technology includes assay devices generated using photolithography as well as other techniques. However, the disclosed assay devices may now be fabricated via direct printing of hydrophobic and/or other substances onto paper. In particular, certain laser and/or inkjet printers can deposit and/or pre-deposit wax, gelatin, and/or other substances directly onto paper at low cost. Other techniques for deposition of the substances may be used.

For example, the design of the devices may be first prepared on a computer, the pattern may then be printed in wax, gelatin, and/or other substances onto paper using a commercially available printer, and the paper may then be heated to a temperature above the melting point of the material(s) so the material(s) reflows and creates hydrophobic barriers that span the thickness of the paper. Once a device is fabricated, reagents may be loaded onto the devices by applying solution(s) of reagent(s) onto the device and allowing related solvent(s) that carried the reagent(s) to evaporate.

In addition to patterning individual layers of paper, stacking multiple layers of patterned paper to create three-dimensional (3D) microPADs may be possible. The layers in the 3D devices may be held together using either a manifold or adhesives. Other substances besides paper may be used.

In sum, aspects of the subject technology are intended to enable modest, cost-effective, at-home diagnostic devices for the reliable quantitation of female reproductive hormones and/or other analytes at femtomolar concentrations using biomatrix barriers via four key steps: (i) selection of an analyte and concomitant displacement of an activator, (ii) activation of an amplifier, (iii) degradation or modification of a biomatrix barrier, and (iv) generation of a signal for read-out.

Some versions of the assay device according to the subject technology may include six layers of wax-patterned WHATMANN® N° 1 CHR or other porous membranes that may be successfully overlaid and stacked. Uniform contact between the successive layers in the device may be achieved by sandwiching them between a plastic frame, which may be designed and built utilizing 3D printing technology.

A top layer of the device may incorporate the sample zone and the read-out well. Fluid added to this zone may wick into the second and third layers, where the analyte may displace enterokinase (the activator) via disruption of covalent or non-covalent selective interactions, such as immunoselection, DNA hybridization, aptamer selection, covalent linkages or magnetic affinity.

The displaced enterokinase may wick into a fourth layer, where it may catalytically convert trypsinogen to trypsin leading to a significant amplification of the amount of trypsin compared to the original amount of analyte. The resulting trypsin may then wick into a fifth layer, where it may digest the biomatrix barrier made of gelatin, thus allowing fluid to wick through the fifth layer and into a sixth layer.

Once fluid enters a sixth layer, the fluid may wick across a channel in the sixth layer, dissolving an indicator and transporting the indicator back up through the first five layers in the device until it reaches the readout well in the top layer. The time from addition of sample to the appearance of the indicator in the read-out well may serve as the signal for the assay. This signal may be expected to be inversely proportional to the concentration of analyte in the sample.

In some aspects, multiple-channel zones may be incorporated on a single device for the simultaneous detection of many analytes. In addition, a branched sample zone may be designed to deliver sample(s) to multiple detection layers for the simultaneous detection of analytes from a single sample-addition step.

Further details of some of the layers discussed above are presented below. The subject technology is not limited to these details.

A sample containing unknown concentrations of analyte may be loaded into or onto a zone or zones on a top layer of the assay device. The sample may encounter a layer of biotynilated analyte pre-bound to anti-analyte antibodies. The anti-analyte antibodies may be coupled to magnetic beads in the second or another layer of the device. Preferred sizes for the magnetic beads are 2.8-1.0 um. Other size beads may be used.

Upon reaching a ligand-binding zone in a next layer of the device, the analyte if present in the sample may compete with the Bt-analyte resulting in an analyte concentration dependent equilibrium of free Bt-analyte. In some aspects, interchangeability of different anti-analyte antibodies coupled to magnetic beads may allow for appropriate immune selection of the desired analyte (e.g., the desired hormone or other analyte to be detected) without significant device design changes.

Preparation of Bt-analyte may be achieved using commercially available biotin conjugation kits and preferably one-step biotynilation reactions. The preparation of Bt-analyte bound magnetic beads may be achieved by pre-binding analyte specific antibodies ($\alpha$-analyte) that are commercially available to magnetic beads. The antibody-linked beads may be incubated with an excess concentration of Bt-analyte in solution to saturate the antibodies. Excess unbound Bt-analyte may then be removed using successive washes.

Deposition and fixing of the Bt-analyte-saturated magnetic beads may be achieved by a simple modification to the paper zone-well. Concentric rings of magnetic toner may be printed within the wax border of the test-well, serving as a surface binding agent for affixing and achieving proper alignment of the magnetic beads. Concomitant with the temporal release of Bt-analyte from the second layer, the initiation of a second ligand specific competitive release may ensue. A layer of desthiobiotinylated-enterokinase (DBt-EK) pre-bound to streptavidin-coated magnetic beads may be affixed to the paper-well by printing concentric rings of magnetic toner.

In some aspects, immuno-selection of analyte may be achieved by competition and release of pre-bound Bt-Analyte to α-analyte which in turn may be covalently bound to magnetic beads affixed to concentric rings of magnetic toner on the device.

The DBt-EK may be loosely bound to streptavidin coated magnetic beads and affixed as above. Desthiobiotin is understood to be a small molecular tag with biotin-like specificity to streptavidin but with a significantly lower affinity (Streptavidin-Biotin Kd≈1×10-14 mol/L, Streptavidin-Desthiobiotin Kd≈1×10-11 mol/L). Taking advantage of the differing dissociation constants of these small molecules, the released Bt-analyte may in turn displace the lower affinity magnetic bead bound DBt-EK.

Enterokinase (a.k.a. Enteropeptidase) is a serine protease that exhibits "trypsin-like activity" and is the primary effector enzyme of pancreatic digestive enzymes in-vivo. Enterokinase displays high affinity and activation of trypsinogen to trypsin (kcat/Km=630 mM−1S−1). A variety of species-derived enterokinase are available commercially. Modification of the enterokinase with desthiobiotin may be achieved with commercially available desthiobiotinylating reagents and purified. Streptavidin-linked magnetic beads are commercially available.

The released DBt-EK from a third layer may have direct access to the fourth layer, which may contain a high concentration of trypsinogen (the inactive precursor of the pancreatic enzyme trypsin). The enterokinase may cleave trypsinogen to convert it to its active form trypsin. A unique property of trypsin (a serine protease) is that it possesses "autocatalytic" activity (Km=4.8 μM and Kcat=74 s−1). The trypsin that may be activated by DBt-EK may in turn set off a cascade of activation by cleaving the remaining trypsinogen on the fourth layer resulting in high concentrations of activated trypsin on the device and a significant increase in the amount of trypsin compared to the initial amount of analyte.

Trypsinogen may be readily deposited onto the paper device by directly pipetting 1.5 μl of a 10 mg/ml trypsinogen solution and allowing it to dry for 24 hrs. Other deposition techniques may be used.

Because trypsinogen is a zymogen (enzyme in its inactive form), this enzyme is expected to remain viable on paper for extended periods of time. Dried trypsinogen has been seen to display excellent longevity of over three months. Alternatively, inactive trypsinogen may be deposited directly to the paper device and dried in place.

A biomatrix barrier may be formed with the deposition of various biologically and non-biologically derived molecules and/or polymers (e.g., gelatin, chitosan, alginic acid, agar, agarose, etc.). This metastable barrier preferably prevents passage of solute until appropriate amplification of trypsin has been achieved.

A chronometric indicator dye may be pre-deposited on the bottom channel. When the above biomatrix is disrupted, the solute may transport the indicator dye in a time-dependent manner to the top layer, resulting in a color change at the read-out well.

To create a solute barrier that may be penetrated only in the presence of analyte (resulting in the subsequent activation and amplification of trypsin), yet resistant to all other conditions, a small pinhole (~1.5 mm diameter) may be incorporated into the fifth layer and saturated with the biomatrix. Pinholes may also be included in the other layers. Other enzyme-degradable biopolymers may also be used to form the biomatrix in the fifth layer.

Gelatin has been used successfully. Varying concentrations of biomatrix have been tested to verify resilience at blocking multiple solutions (PBS, TBS, and commercially available plasma, saliva, urine) for periods of time >1.5 hrs. Gelatin may be a mixture of peptides and proteins derived from hydrolyzed collagen. Upon solidification, gelatin forms a hydrophobic barrier on paper that provides phenomenal longevity.

As the active-trypsin reaches this biomatrix barrier, it preferably proceeds to hydrolyze proteins and peptides at their C-terminal Lysine and Arginine residues. The ensuing hydrolysis of the biomatrix results in increased porosity, followed by passage of solvent through the barrier. The observed time-dependent passage of solvent through the device may be a result of the enzyme concentration dependent hydrolysis of the biomatrix.

A simplified version of the device comprising only some layers described above may be used. The zymogen to the enzyme capable of degrading the polymer may be added to the fourth layer or some other layer, and test solutions containing various concentrations of the zymogen's activator enzyme may be added to the device to test the capabilities of the biomatrix. The ability to use different biopolymers may allow for the development of assays that are completely orthogonal and do not interfere with each other.

The last layer of this 3-D device preferably corresponds to the deposition of an indicator dye, which may be pre-dried on a small horizontal channel connecting the vertical loading channels to the vertical read-out channel. When the biomatrix is disrupted, the sample solution preferably wicks into the bottom layer, dissolves the indicator, and transports the indicator via wicking to the top layer resulting in a color change at the read-out well. In some aspects, failure of this indicator dye to reach the read-out well may correlate to a negative signal (i.e., absence of a target analyte).

Further information regarding aspects of the subject technology is disclosed in a document titled "RUI: Chronometric quantitation of female reproductive hormones at low-picomolar concentrations on paper-based biomatrices" (the "Incorporated Document"). The Incorporated Document is included as an Appendix to this filing and is hereby incorporated by reference as if fully set forth herein. The subject technology is not limited by the information in the Incorporated Document. Rather, additional disclosures in the Incorporated Document represent expansions of the subject technology.

The subject technology is described further below with respect to the drawing figures. The technology is not limited to the subject matter disclosed in the drawing figures, which are provided for illustrative purposes.

FIG. 1 illustrates aspects of the subject technology arranged in a generally two-dimensional structure for lateral flow. Assay device 100 preferably is made of paper with the various zones described herein generated via printing technology.

In FIG. 1, zone 101 is a region defined for deposition of a sample that may contain an analyte of interest. The zone preferably includes a high concentration of a zymogen (an enzyme in an inactive state that may be activated by an activator enzyme). Channel 102 provides communication with zone 103, preferably via wicking. Zone 103 preferably includes a biopolymer that forms an aqueos impermeable or semipermeable barrier that may be degraded or modified enzymatically to allow fluid to wick through.

Channel 104 permits communication from zone 103 to zone 105, for example as described above. In FIG. 1, zone 105 includes a readout zone that indicates presence of the target analyte in the sample.

When a preferably aqueous sample containing a target analyte is introduced into zone 101, the analyte directly or indirectly activates the zymogen. The zymogen preferably acts as an amplifier for the analyte. Details of possible reactions for such amplification are disclosed above.

The analyte, amplified analyte, and/or resulting substance degrades the barrier in zone 103. In preferred aspects, the degradation is enzymatic. Water, the analyte, amplified analyte, and/or resulting substance then wicks through channel 104 to zone 105. That zone preferably includes a dye or other visual indicator that reacts to the presence of water, the analyte, amplified analyte, and/or resulting substance to generate a visual indication of the analyte's presence in the sample. For example, the zone may include a preferably small molecule dye that changes color when wet.

Indicators other than visual ones may also be used. For example but without limitation, zone 105 may change resistance, conductivity, and/or other properties in the presence of water, the analyte, amplified analyte, and/or resulting substance.

A time between addition of a sample to zone 101 and a resulting indication in zone 105 preferably serves as a chronometric signal for presence of the analyte in the sample. The time of an indication expressing in zone 105 has been seen to be proportional to the concentration of activator enzyme in the sample. The subject technology is not limited to this result.

Figure 2:
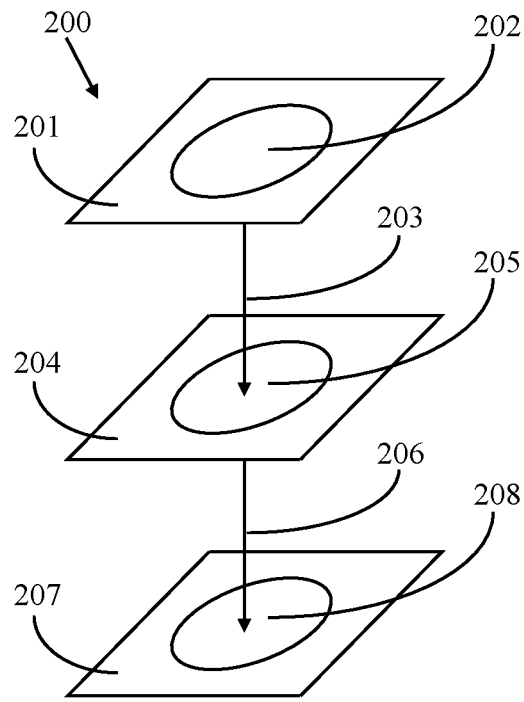
FIG. 2 illustrates aspects of the subject technology arranged in a generally three-dimensional structure.

FIG. 2 illustrates aspects of the subject technology shown in FIG. 1 arranged in a generally three-dimensional structure for vertical flow. Assay device 200 preferably is made of layers of paper with the various zones described herein generated via printing technology.

In FIG. 2, layer 201 includes zone 202 defined for deposition of a sample that may contain an analyte of interest. The zone preferably includes a high concentration of a zymogen. Line 203 represents communication, preferably via wicking, with layer 204 including zone 205. Zone 205 preferably includes a barrier that may be degraded to allow fluid to wick through. In preferred aspects, the degradation is enzymatic. Line 206 represents communication, again preferably through wicking, with layer 207 including zone 208. In FIG. 2, zone 208 includes a read-out zone.

Figure 3:
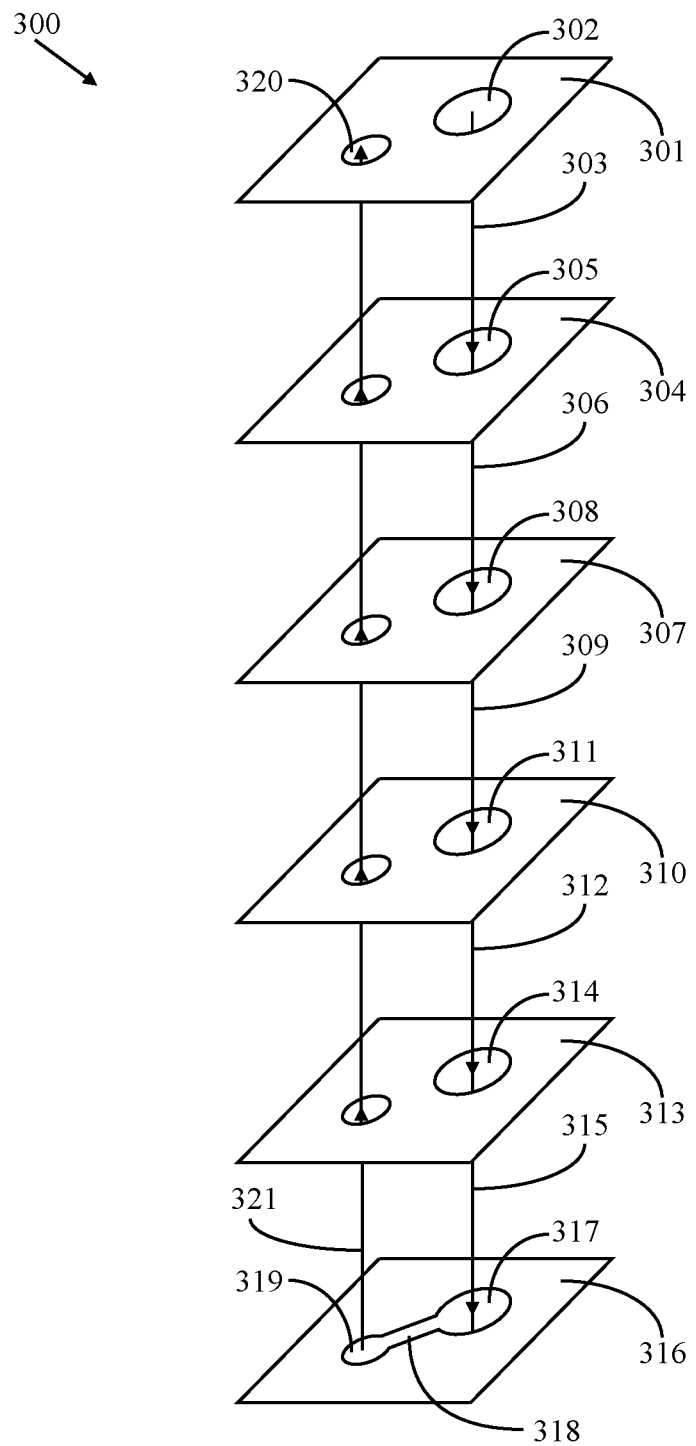
FIG. 3 illustrates additional aspect of the subject technology arranged in a generally three-dimensional structure.

FIG. 3 illustrates additional aspects of the subject technology arranged in a generally three-dimensional structure. Specific details of certain chemical reactions are included in the description of assay device 300. The subject technology is not limited to these additional aspects and details.

Assay device 300 includes several layers, which preferably are paper layers on which various substances have been deposited. Layer 301 includes zone 302 for introduction of a sample that may contain a target analyte. The circle around zone 302 may be a printed circle to identify where the sample should be deposited.

Line 303 represents communication to next layer 304. In the description of FIG. 3, all communication may be via wicking, other capillary action, or some other process.

Ligand-binding zone 305 in layer 304 preferably includes a layer of biotynilated analyte pre-bound to anti-analyte antibodies. The anti-analyte antibodies may be coupled to magnetic beads, for example as discussed with respect to FIG. 4.

Line 306 represents communication to next layer 307, for example via wicking. Zone 308 in layer 307 may include Desthiobiotinylated-enterokinase (DBt-EK). The DBt-EK may result in a second ligand specific competitive release. In some aspects, the DBt-EK may be loosely bound to a precursor such as streptavidin. The precursor may be coated on magnetic beads and/or otherwise affixed as further discussed with respect to FIG. 4.

Line 309 represents communication to another layer 310 with zone 311. Zone 311 may contain a high concentration of an amplifier such as trypsinogen.

Line 312 represents communication with layer 313 including zone 314. That zone preferably includes a biomatrix barrier formed of substances such as biologically derived molecules and/or polymers (e.g., gelatin, chitosan, agar, agarose, alginic acid etc.). This metastable barrier preferably prevents communication to the next layer until appropriate amplification has been achieved.

Line 315 represents communication with layer 316 including zone 317, which preferably includes a pre-deposited indicator dye. When the biomatrix in the above layers is disrupted, the indicator may be activated in a time-dependent (i.e., chronometric) manner related to an amount of the analyte in the sample and/or the amplification thereof. The activated indicator dye preferably communicates through channel 318 to zone 319 when activated. The channel may be defined by deposition of barriers along the sides of the channel or may be undefined.

If activated, the indicator may communicate through the device to view well 320 as indicated by line 321. In alternative embodiments, the indicator dye also and/or instead may reside in channel 318, zone 319, the path indicated by line 321, or some combination thereof.

Figure 4:
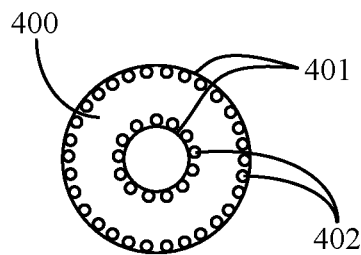
FIG. 4 illustrates a magnetic bead arrangement that may be used with the subject technology, for example aspects illustrated in FIG. 3.

FIG. 4 illustrates a magnetic bead arrangement that may be used with the subject technology, for example aspects illustrated in FIG. 3. Zone 400 includes concentric rings 401 that may be printed to form the zone. While two concentric rings are shown, any number of rings may be used. In addition, shapes other than rings may be used.

Magnetic beads 402 may be deposited onto and/or into the zone after the rings are created. Alternatively, the rings and/or other structures defining the zone may be directly created with the magnetic beads, for example via printing with magnetic toner. The beads may be saturated with, coated with, contain, or otherwise enable incorporation of Bt-analyte, DBt-EK, other substances, or some combination thereof into assay devices according to aspects of the subject technology.

The number of magnetic beads illustrated in FIG. 4 is for illustrative purpose only. More or fewer magnetic beads may be used. In most aspects, far more magnetic beads will be present. Furthermore, the magnetic beads may be used on various layers and for other purposes, for example for incorporation of a magnetically active indicator dye into the assay device.

Figure 5:
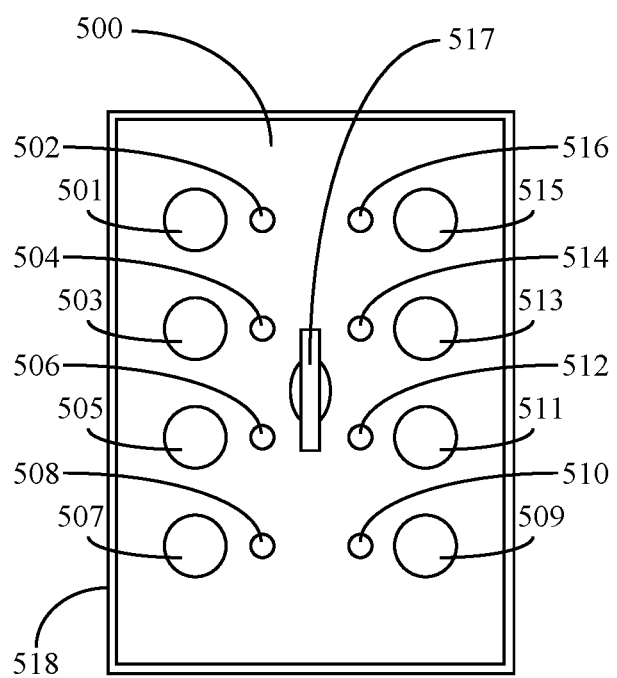
FIG. 5 illustrates aspects of the subject technology in a multi-zone configuration.

FIG. 5 illustrates aspects of the subject technology in a multi-zone configuration. Device 500 includes multiple zones 501, 503, 505, 507, 509, 511, 513, and 515 for application of a sample that may contain an analyte of interest. Corresponding view wells 502, 504, 506, 508, 510, 512, 514, and 516 are associated with those zones. Each of the paired zones for samples and view wells may be constructed and operate as described above.

Alternatively, a zone for application of a sample may communicate with multiple view wells. The communication to those view wells may include different concentrations of substances resulting in different chronometric results based upon concentration of an analyte of interest in a sample.

In some aspects, fastener 517 may be used to hold device 500 together. In addition, preferably frame 518 may be used. For example, a plastic frame may be used to hold device 500 together.

The invention may be in no way limited to the specifics of any particular embodiments and examples disclosed herein. For example, the terms "aspect," "example," "e.g.," "preferably," "alternatively," "may," "potential," and the like denote features that may be preferable but not essential to include in some embodiments of the invention. For additional examples, the subject technology may be implemented using materials other than paper (e.g., plastic), and the various zones and wells may be defined using techniques other than printing (e.g., imprinting, cutting, stamping, etc.).

Details illustrated or disclosed with respect to any one aspect of the invention may be used with other aspects of the invention. Additional elements and/or steps may be added to various aspects of the invention and/or some disclosed elements and/or steps may be subtracted from various aspects of the invention without departing from the scope of the invention. Singular elements/steps imply plural elements/steps and vice versa. Some steps may be performed serially, in parallel, in a pipelined manner, or in different orders than disclosed herein. Many other variations are possible which remain within the content, scope, and spirit of the invention, and these variations would become clear to those skilled in the art after perusal of this application.

The invention claimed is:

1. An assay device comprising:
    a loading zone for a sample solution that may contain an analyte;
    at least one enzyme in communication with the loading zone from which at least one enzyme is displaced by presence of the analyte;
    an amplifier in an inactive state in communication with the at least one enzyme that becomes activated in the presence of the at least one enzyme;
    a semi-permeable biomatrix barrier comprising a biopolymer comprising proteins, peptides or carbohydrates or a mixture thereof in communication with the activated amplifier that is hydrolyzed by said activated amplifier and is degraded or has increased porosity;
    a porous membrane in contact with said biomatrix barrier, which when said biomatrix barrier is degraded or has increased porosity, said porous membrane wicks said solution to an indicator; and
    said indicator responsive to the solution, which in turn reflects a concentration of the analyte in the sample solution loaded on the device.

2. The assay device as in claim 1, wherein the at least one enzyme comprises enterokinase or enterokinase conjugated to another molecule.

3. The assay device as in claim 1, wherein the amplifier comprises a zymogen that becomes activated by the at least one enzyme.

4. The assay device as in claim 3, wherein the amplifier comprises trypsinogen.

5. The assay device as in claim 1, further comprising magnetic beads coupled with the at least one enzyme.

6. The assay device as in claim 1, wherein the biopolymer is collagen, gelatin, chitosan, alginic acid, agar or agarose.

7. The assay device as in claim 1, wherein the loading zone, the activator, the amplifier, the biomatrix barrier, the indicator, or some combination thereof are disposed on paper or other porous membrane layers.

8. The assay device as in claim 7, further comprising a frame that holds the layers in communication with each other.

9. The assay device as in claim 1, further comprising one or more additional loading zones, associated enzymes, associated selective reagents, associated amplifiers, associated biomatrix barriers, or associated indicators.

10. The assay device as in claim 9, wherein one or more of the additional loading zones, the associated at least one enzyme, the associated selective reagents, the associated amplifiers, the associated biomatrix barriers, the associated indicators, or some combination thereof are calibrated to show indications at different times or different intensities based on the concentration of the analyte present in the sample.

11. An assay method comprising:
    accepting a sample solution on an assay device that may contain at least one analyte into at least one loading zone;
    communicating the sample solution to at least one enzyme with the at least one enzyme displaced by presence of the analyte;
    activating at least one amplifier in the presence of the at least one enzyme;
    degrading or increasing porosity of a semi-permeable biomatrix barrier comprising a biopolymer comprising proteins, peptides, carbohydrates or a mixture thereof by the activated amplifier;
    said biomatrix barrier that is degraded or has increased porosity in contact with a porous membrane that wicks said solution to an indicator, which in turn reflects a concentration of the analyte in the sample loaded on the device.

12. The method of claim 11, wherein the displacement of the at least one enzyme relies on use of non-covalent interactions.

13. The assay method as in claim 11, wherein the selection of the analyte or displacement of the at least one enzyme relies on use of non-covalent interactions.

14. The assay method as in claim 13, wherein the at least one enzyme comprises enterokinase or enterokinase conjugated to another molecule.

15. The assay method as in claim 11, wherein the amplifier comprises a zymogen that becomes activated by the at least one enzyme.

16. The assay method as in claim 11, wherein the amplifier comprises trypsinogen and becomes activated to trypsin by at least one enzyme comprising enterokinase.

17. The assay method as in claim 11, wherein the biopolymer comprises gelatin, chitosan, alginic acid, agar or agarose.

18. The device of claim 1, wherein said at least one enzyme comprises enterokinase and said amplifier comprises trypsinogen.

19. The device of claim 18, wherein said biomatrix barrier comprises collagen or gelatin.

20. The device of claim 1, wherein said analyte is biotinylated and bound to anti-analyte molecules selected from the group consisting of anti-analyte antibodies, anti-analyte aptamer and anti-analyte M13 phage, said enterokinase comprises desthiobiotinylated enterokinase, said amplifier comprises trypsinogen and said biomatrix barrier comprises a biologically derived polymer.

21. The device of claim 19, wherein said biotinylated analyte is bound to anti-analyte antibodies.

22. The method of claim 11, wherein said biomatrix barrier comprises collagen or gelatin.

23. The device of claim 20, further comprising magnetic beads coupled to said antibody, magnetic beads coupled to said desthiobiotinylated enterokinase, or both magnetic beads coupled to said antibody and magnetic beads coupled to said desthiobiotinylated enterokinase.

24. An assay device comprising:
a loading zone for a sample that may contain an analyte that is biotinylated and bound to anti-analyte molecules selected from the group consisting of anti-analyte antibodies, anti-analyte aptamer and anti-analyte M13 phage;
at least one desthiobiotinylated enterokinase in communication with the loading zone from which said at least one enterokinase is displaced by presence of the analyte;
an amplifier in an inactive state in communication with the at least one enterokinase that becomes activated in the presence of the at least one enterokinase;
a semi-permeable biomatrix barrier comprising a biopolymer comprising proteins, peptides, carbohydrates or a mixture thereof in communication with the activated amplifier that is hydrolyzed and is degraded or modified has increased porosity by said activated amplifier; and
an indicator responsive to the degradation or modification of the biomatrix barrier, which in turn reflects a concentration of the analyte in the sample loaded on the device, said device comprising a first layer of paper compromising said loading zone and a well for examining said indicator, a second layer comprising said biotinylated analyte coupled to said anti-analyte antibody, a third layer comprises said at least one enterokinase, a fourth layer comprising said trypsinogen, a fifth layer comprising said biomatrix barrier, and a sixth layer comprising said indicator.

25. The device of claim 24, wherein said first layer comprises a well in communication with said indicator.

26. The device of claim 24, wherein said fifth layer comprises a hole.

27. The device of claim 1, wherein said biopolymer comprises peptides, proteins or a mixture thereof derived from collagen or hydrolyzed collagen.

28. The device of claim 1, wherein said inactive amplifier comprises a zymogen and is autocatalytic.

29. The device of claim 1 in which said indicator reflects concentration of the analyte as a measurement of the time it takes for the solution to move from the loading zone to the indicator.

30. The method of claim 11, in which the time it takes for the solution to move from the loading zone to the indicator reflects a concentration of the analyte in the sample solution loaded on the device.

* * * * *